US006455264B1

(12) United States Patent
Baumeister et al.

(10) Patent No.: US 6,455,264 B1
(45) Date of Patent: Sep. 24, 2002

(54) ANTIBODIES AND DIAGNOSTIC METHODS FOR THE DIAGNOSIS OF PESTIVIRUSES

(75) Inventors: Judith Baumeister; Robert Stark, both of Wuppertal; Matthias König, Schönbach; Heinz-Jürgen Thiel, Giessen, all of (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/498,848

(22) Filed: Feb. 7, 2000

(30) Foreign Application Priority Data

Feb. 12, 1999 (EP) ............................................. 99200430

(51) Int. Cl.[7] ........................ G01N 33/53; G01N 33/537
(52) U.S. Cl. ............................. 435/7.1; 435/5; 435/7.9; 435/7.92; 435/339; 435/810; 530/388.1; 530/388.3
(58) Field of Search .............................. 435/5, 7.1, 7.9, 435/7.92, 7.93, 7.94, 810, 339, 70.21; 530/388.1, 388.3

(56) References Cited

U.S. PATENT DOCUMENTS 6,174,667 B1 * 1/2001 Huchzermeier et al. ....... 435/5

OTHER PUBLICATIONS

Kosmidou et al., "Differentiation of Classical Swine Fever Virus (CSFV) Strains Using Monoclonal Antibodies Against Structural Glycoproteins," Veterinary Microbiology, 1995, vol. 47 (1–2), pp. 111–118.

Hulst et al., "Inactivation of the RNase Activity of Glycoprotein Erns of Classical Swine Fever Virus Results in a Cytopathogenic Virus," Journal of Virology, 1998, vol. 72, No. 1, pp. 151–157.

Bruschke et al., "Glycoprotein Erns of Pestiviruses Induces Apoptosis in Lymphocytes of Several Species," Journal of Virology, 1997, vol. 71, No. 9, pp. 6692–6696.

Windishch et al., "RNase of Classical Swine Fever Virus: Biochemical Characterization and Inhibition by Virus–Neutralizing Monoclonal Antibodies," Journal of Virology, 1996, vol. 70 (1), pp. 352–358.

Fritzemeier et al., "Experimentally Induced "late–onset" Mucosal Disease—Characterization of the Cytopathogenic Viruses Isolated," Veterinary Microbiology, 1995, vol. 46 (1–3), pp. 285–294.

Bouma et al., "Determination of the Onset of the Herd–Immunity Induced by the E2 Sub–Unit Vaccine Against Classical Swine Fever Virus," Vaccine, 2000, vol. 18, No. 14, pp. 1374–1381.

* cited by examiner

*Primary Examiner*—Laurie Scheiner
(74) *Attorney, Agent, or Firm*—Mark W. Milstead; William M. Blackstone

(57) ABSTRACT

The present invention relates to a diagnostic method for the diagnosis of Pestivirus infection in animals, in particular to a method for the diagnosis of animals infected with BVDV. A monoclonal antibody directed to a conserved antigen determinant on the Pestivirus $E^{RNS}$ protein is provided which allows the identification of infected animals with a high sensitivity and specificity.

10 Claims, 1 Drawing Sheet

ANTIBODIES AND DIAGNOSTIC METHODS FOR THE DIAGNOSIS OF PESTIVIRUSES

BACKGROUND OF THE INVENTION

Figure 1:
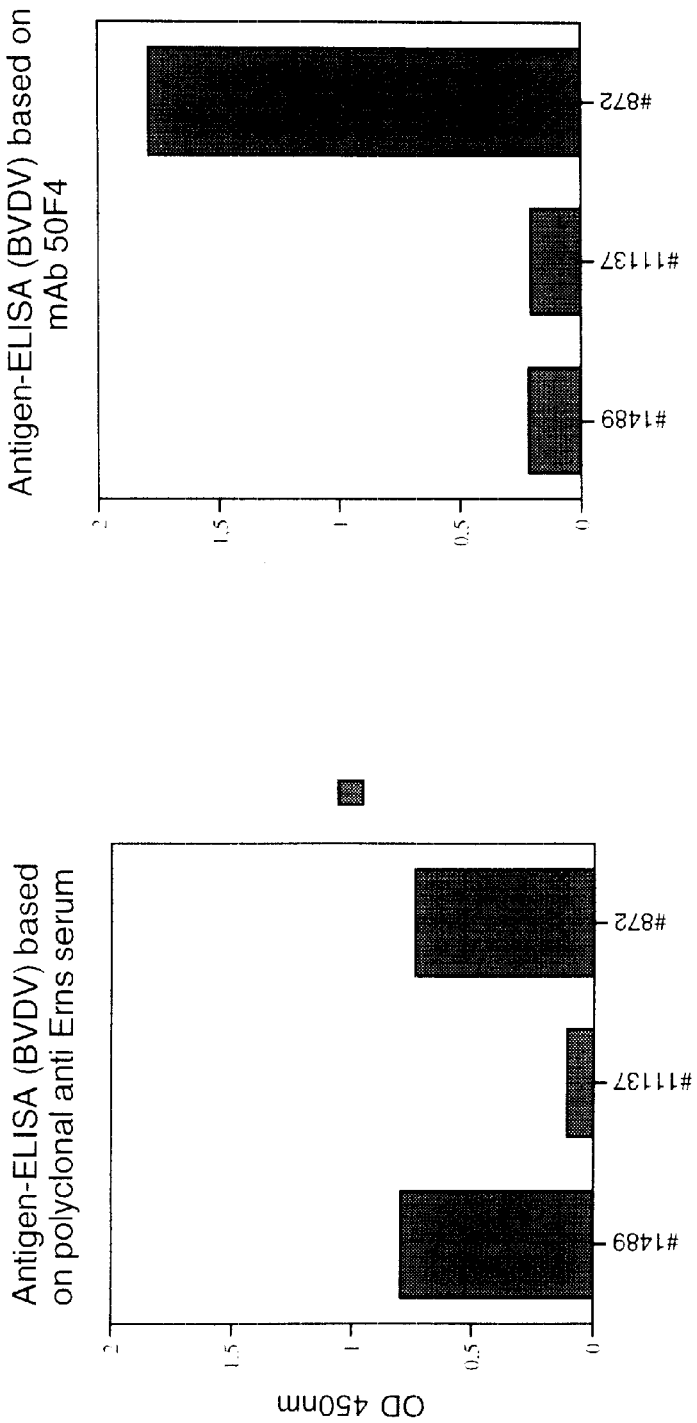

The genera Pestivirus, Flavivirus and "hepatitis C virus group" constitute the family Flaviviridae. The genus Pestivirus currently comprises three members, bovine viral diarrhoea virus (BVDV), classical swine fever virus (CSFV), and border disease virus (BDV). The presence of a fourth separate group of Pestiviruses comprising isolates from cattle and sheep has been recently described, and it is now generally accepted to refer to this additional species as BVDV-2; consequently, classical BVDV strains are named BVDV-1. BVDV-1 and BVDV-2 are considered world-wide as important pathogens of cattle. Both can cause acute infections (diarrhoea, fever, hemorrhagic syndrome) as well as abortion, malformation, and persistent infection. Persistently infected animals represent the major reservoir of the virus; such animals may come down with fatal mucosal disease (MD). With regard to economical impact the reproductive losses are most significant. The assay outlined below aims at the identification of infected and especially persistently infected animals. In control programs established in some countries persistently infected animals are removed in order to obtain BVDV free herds.

Persistently infected animals are generated by the infection of a foetus with a non-cytopathogenic (noncp) BVDV strain during the first trimester of gestation. Such animals acquire immunological tolerance to the particular noncp strain (no antibodies against the persisting virus detectable). The persistently infected animals shed virus in considerable amounts during their life and represent the main reservoir for BVDV. Persistently infected animals may be born without clinical symptoms. Therefore, the identification and eradication of persistently infected animals is an important goal in the control of the disease.

Boulanger et al. (J. Gen. Virol. 72, 1195–1198, 1991) and Corapi et al. (Am. J. Vet. Res. 51, 1388–1394, 1990) disclose the characterisation of a large number of anti-BVDV monoclonal antibodies (Moabs). Most of these Moabs do not recognise an antigen determinant present on all BVDV strains under examination. Corapi et al. identified one Moab which is reactive with a linear antigen determinant expressed by all tested BVDV strains. No diagnostic application of these Moabs is suggested in these documents.

For the diagnosis of BVDV infection in cattle, several methods are available in the art. Until now, the detection of BVDV is sometimes performed by means of the "tissue culture method" in which leukocytes are prepared from blood samples and inoculated on susceptible cells. Infection of the cells by BVDV is detected by immunostaining techniques using specific serological reagents. This diagnostic method is considered as the "golden standard" with regard to specificity and sensitivity. However, this method is quite laborious, time consuming, cannot be automated and is thus not applicable to very large numbers of samples.

Antigen-capture ELISAs have become commercially available for BVDV detection and these assays overcome some of the disadvantages associated with the tissue culture method (Brinkhof et al., Veterinary Microbiology 50, 1–6, 1996; Fritzmeier et al., AFT-Tagung BVD-Bekämpfung, October 1998, Hannover, Germany).

The set up of all these commercially available assays is: (a) coating of microtiter plates with monoclonal antibodies (Moabs) or polyclonal monospecific antiserum against the non-structural protein NS2/3 for capturing of antigen, (b) detection of the viral antigen after incubation with a sample (obtained from leukocytes or organ samples) by either a Moab or polyclonal monospecific antiserum. The sensitivity of the available assays turned out to be less than 100%. Moreover, the presently available assays require the use of leukocyte preparations of anti-coagulated blood, anti-coagulated blood or tissue samples from organs of the test animals.

BVDV antigen detection by means of FACS (fluorescence activated cell sorter) analysis has also been described. This technique also uses leukocytes and BVDV infected cells are identified with antibodies against the BVDV NS2/3 antigen. This diagnostic method is generally considered comparable to infection of culture cells. This method also requires the preparation of blood and the availability of highly specialised laboratory equipment is required.

Thus, there exists a need for a sensitive, rapid and practical diagnostic method for determining Pestivirus infection in animals, in particular for determining BVDV infection in cattle, especially in the framework of eradication programs where large numbers of cattle are to be monitored.

Moreover, there is a need for a diagnostic reagent for use in such diagnostic methods which is highly specific (i.e. no false positive samples) and highly sensitive (no false negative samples).

DETAIL DESCRIPTION OF THE INVENTION

To that aim the present invention provides in a first aspect a monoclonal antibody which is capable of specifically binding to an $E^{RNS}$ antigen determinant of a Pestivirus which either is or cross-competes with a monoclonal antibody expressed by hybridoma cell line 50F4-10-INT, deposited at the ECACC, Salisbury, UK, on Feb. 5, 1999 under accession no. 99020505.

It has been found that a monoclonal antibody according to the invention recognises a very conserved epitope on the $E^{RNS}$ (RNS=ribonuclease soluble) protein of all tested Pestiviruses, including many different BVDV, CSFV and BDV strains. Detection of the Pestivirus encoded glycoprotein $E^{RNS}$ (or antibodies against this glycoprotein) in a test sample indicates that the animal from which the test sample is derived is infected with the virus. Moreover, it has been found that a monoclonal antibody according to the invention is highly specific, i.e. the monoclonal antibody is able to discriminate between negative and positive samples from animals, such as cattle, in contrast to a polyclonal monospecific $E^{RNS}$ antiserum.

The $E^{RNS}$ protein represents a structural glycoprotein and as such forms part of the Pestivirus. In addition it is secreted from infected cells (for example leukocytes) leading to a soluble form of $E^{RNS}$. Accordingly, both forms of $E^{RNS}$-soluble as well as the virus-associated form—are present in cells as well as serum/plasma of infected animals. This is in contrast to the NS2/3 protein which is only detectable in infected cells (Colett et al., Virology 165, 191–199 and 200–208, 1988; Thiel et al., J. Virology 65, 4705–4712, 1991; Weiland et al., J. Virology 66, 3677–3682, 1992; Meyers et al., Advances in Virus Research 47, 53–118, 1996; Rümenapf et al., J. Virology 67, 3288–3294, 1993).

A monoclonal antibody that cross-competes with the specifically deposited monoclonal antibody is an antibody that binds to the same conserved (conformational) antigen determinant as the deposited monoclonal antibody. Cross-competition experiments are relatively easy to carry out (Waters et al., Virus Res., 22, 1–12, 1991) and so it is a straightforward matter to determine whether a given antibody cross-competes with the monoclonal antibody specifically referred to above.

Briefly, such cross-competing monoclonal antibodies reactive with the same conserved antigen determinant can be obtained by using a spectrum of defined pestiviruses for screening after immunisation of mice with pestivirus infected cells, purified virus or, preferably, purified $E^{RNS}$ protein (Wensvoort et al., J. Gen. Virol. 71, 531–540, 1990; Hulst et al., Virology 200, 558–565, 1994), followed by fusion. First, monoclonal antibodies are selected which react with an antigen determinant present on all pestivirus strains under examination. Subsequently, the selected monoclonal antibodies can be used in a standard competition ELISA with the deposited monoclonal antibody ECACC no. 99020505 to identify monoclonal antibodies which bind to the same conserved antigen determinant as the deposited Moab.

The monoclonal antibody technology has become well established since the original work by Kohler and Milstein (Nature, 256, 495, 1975) and there are today many available protocols for the routine generation of monoclonal antibodies. Suitable techniques, for example, are those of Gefter et al., (Somatic Cell Genetics, 3, 231, 1977), Kohler et al., (Eur. J. Immunol. 6, 292–295, 1976) and Goding ("Monoclonal antibodies: Principles and Practice"; 3rd Edition, 1996, Academic Press, New York).

Typically, the protocol used is as follows:
- an experimental animal (such as a mouse) is immunised challenged with the antigen against which antibodies are to be raised;
- the spleen cells of the animal are then fused to cells of a myeloma cell line, and the resultant hybridoma fusion cells plated out on selective medium;
- screening for specific antibodies is undertaken by any suitable technique, for example by the use of anti-immunoglobulin antibodies from another species.

Preferably, the present invention provides a monoclonal antibody which is capable of specifically binding with a conserved antigen determinant on the Pestivirus $E^{RNS}$ protein, and which is the monoclonal antibody expressed by the hybridoma cell line deposited at the ECACC under accession no. 99020505.

According to a second aspect of the present invention, there is provided a hybridoma cell line capable of expressing (and preferably secreting) a monoclonal antibody as described above. The generation of hybridoma cell lines and the identification of a hybridoma cell line expressing the monoclonal antibody according to the present invention has been described above.

A preferred hybridoma cell line according to the invention is the cell line 50F4-10-INT, deposited at the ECACC under accession no. 99020505.

The advantageous properties of a monoclonal antibody according to the invention, i.e. its high specificity and sensitivity, in addition to its reactivity with an antigen determinant which is accessible in a standard immunological assay, make the present monoclonal antibody a very appropriate reagent in a diagnostic assay for identifying Pestivirus infection in animals, in particular for identifying BVDV in (persistently) infected cattle.

Therefore, in a further aspect the present invention provides a method for the diagnosis of Pestivirus infection in animals comprising the step of examining a test sample of an animal suspected of being infected with a Pestivirus for the presence of Pestivirus antibodies or antigens, characterised in that the test sample is contacted with a monoclonal antibody as described above. In view of the fact that the monoclonal antibody according to the invention recognises a conserved epitope present on all tested BVDV, CSFV and BDV strains, the diagnostic method according to the invention is suited for the detection these viruses in all host animals of these viruses, including cattle, swine, sheep and goats.

Preferably, the present invention is directed to a method for the diagnosis of Pestivirus infection in animals as described above in which the presence of BVDV antigens or antibodies in a test sample obtained from cattle is examined.

The design of the immunoassay may vary and can be similar to those immunoassays which are commonly used in the art for identifying the presence of virus antigens or antibodies in samples taken from humans or animals. For example, the assay may be based upon a competition- or direct reaction. Furthermore, protocols may use solid supports or may use cellular material. The detection of the Pestivirus, such as BVDV, antigens or antibodies may involve the use of (directly or indirectly) labelled antibodies and the labels may be enzymes, fluorescent-, chemilumiscent-, radioactive- or dye molecules. The detection antibodies may be $E^{RNS}$ monospecific polyclonal or monoclonal antibodies. In particular, the detection antibody is a (labelled) monoclonal antibody according to the present invention. In the latter case, the Pestivirus antigen may be captured by polyclonal anti-Pestivirus antibodies, in particular mono- specific $E^{RNS}$ antibodies.

Preferably, the method for the diagnosis of Pestivirus infection is an antigen assay which is further characterised in that the test sample is examined for the presence of Pestivirus, in particular BVDV, antigens and comprises the steps of:

(i) incubating the test sample with the monoclonal antibody, (ii) allowing the formation of an antibody-antigen complex, (iii) detecting the presence of the antibody-antigen complex.

In this method the monoclonal antibody according to the invention may bind to the conserved $E^{RNS}$ antigen determinant present in infected cells or in soluble form in plasma or serum in the test sample. Therefore, in principle, the method according to the invention comprises the presently used antigen assays, such as the "tissue culture method", antigen-capture ELISA and FACS analysis referred to above.

In a preferred embodiment the test sample is contacted with the (capture) antibody according to the invention which is coated on a solid support, such as a microtitre plate, a membrane, a test strip or the surface of a particle, such as a latex particle.

Although a leukocyte suspension, whole blood or a tissue sample may be used as the test sample in the method according to the present invention, the present inventors have found that particular good results could be obtained by using serum or plasma of animals suspected of being infected with the BVDV. In case serum or plasma is used as the test sample in the method according to the invention, a method for the diagnosis of BVDV infection is provided which on the one hand is very sensitive and specific and which, on the other hand, is very practical, can be rapidly performed and allows the examination of large numbers of test samples.

Therefore, in an even more preferred embodiment of the invention a method for the diagnosis of Pestivirus infection in animals is provided in which the test sample contacted with the capture monoclonal antibody described above is serum or plasma of the animal, in particular cattle, suspected of being infected.

A particularly suited method for the diagnosis of Pestivirus infection according to the present invention as described above is the well known ELISA.

In an exemplifying ELISA, the wells of a polystyrene micro-titre plate are coated with a monoclonal antibody according to the invention followed by blocking of unoccupied binding sites, for example with skim milk. Next, the wells of the coated plates are incubated with the serum or plasma of the test sample. After the incubation, the presence (or absence) of the antibody-antigen complex is determined by detecting bound $E^{RNS}$ with (e.g. biotin) labelled polyclonal monospecific- or monoclonal antibodies against $ER^5$. The labelled antibody will occupy the free antigen determinants on the Ems protein that have not been occupied by the capture monoclonal antibody. Subsequently, for example, horse radish peroxidase coupled to avidin may be added and the amount of peroxidase is measured by an enzymatic reaction. Alternatively, after the incubation with the test sample, the amount of $E^{RNS}$ antigen present in the serum or plasma may be determined directly by using an anti-$E^{RNS}$ antibody-enzyme conjugate followed by the enzymatic reaction.

The antigen ELISA according to the invention is particularly suited for identifying young animals, i.e. younger than 3 months of age, in view of the fact that the presence of maternal derived antibodies in such animals do not influence the outcome of the test.

In a further aspect of the invention a diagnostic kit is provided which comprises in addition to a monoclonal antibody according to the invention, means for detecting whether the $E^{RNS}$ antigen is bound to the capture monoclonal antibody. The capture monoclonal antibody and the detection means may be provided in separate compartments of the kit. The capture monoclonal antibody is preferably provided bound to a solid support. The detection means comprise a detectable labelled second antibody (monoclonal or polyclonal), which binds to the Pestivirus, preferably BVDV antigen.

According to a further aspect of the present invention, there is provided the use of a monoclonal antibody according to the present invention for the in vitro diagnosis of Pestivirus, in particular BVDV, CSFV and BDV, infection in an animal.

EXAMPLES

Example 1

Production and Selection of (Monoclonal) Antibodies

Preparation of monoclonal antibodies:

The expression of the recombinant protein $E^{RNS}$ was performed via a recombinant baculovirus, which contains the complete gene for the CSFV Alfort Tübingen $E^{RNS}$ (Windisch et al., J. Virology 70, 352–358, 1996; Rümenapf et al., supra; Hulst et al., Virology 200, 558–565, 1994). Purification from extracts of infected insect cells was performed by immuno-affinity with an $E^{RNS}$ specific monoclonal antibody. Female Balb/c mice were immunised with 50 μg purified recombinant $E^{RNS}$ mixed with Freund's adjuvant by the intraperitoneal (i.p.) route. On days 5 to 2 before fusion one selected mouse was boosted with recombinant $E^{RNS}$ (50 μg) without adjuvant every day until fusion. The spleen cells were fused with SP2/0 myeloma cells in the presence of polyethylene glycol. The fusion products were plated into 96-well plates and cultivated in the presence of HAT medium (hypoxanthine, aminopterin, thymidine) for selection of hybrids between myeloma cells and B cells. Hybridomas secreting $E^{RNS}$ specific antibodies were identified by an ELISA as described below. One day before screening the medium in each well was replaced by fresh medium.

Screening of the Hybridomas:

Materials:

ELISA plates: 96-well,

Catching antibody: purified IgG from rabbits that have been immunised with affinity purified $E^{RNS}$ expressed via recombinant baculovirus, containing the gene for the CSFV Alfort Tübingen $E^{RNS}$ was used to coat ELISA plates, Antigen for initial screening: lysate of insect cells infected with the recombinant baculovirus expressing CSFV $E^{RNS}$, Antigens for further characterisation of hybridomas: lysate from PK15 cells infected with different CSFV strains, and lysates from MDBK cells infected with different BVDV/BDV strains, Blocking solution: 1% bovine serum albumin in PBS/ 0.05% Tween 20, Detection antibody: Peroxidase-conjugated donkey antimouse IgG with minimal cross reaction to rabbit serum proteins, ELISA wash buffer: 20 mM Tris-HCl pH 7.4/300 mM NaCl/2.5 mM KCl/0.05% Tween 20, Substrate: stock solution 10mg TMB in 4ml DMSO, Substrate buffer: 100 mM sodium acetate pH 5.6/0.05% Tween 20, Working substrate: 1.2 ml TMB stock plus 8.8 ml substrate buffer plus 1.5 μl 30%H2O2, Stop solution: 1:4 diluted concentrated H2SO4.

Procedure:

Coating: Each well of the ELISA plates was coated with purified rabbit anti $E^{RNS}$ IgG in PBS; coating was performed overnight at 4° C., Blocking: Each well received 200μl of blocking solution; incubation at room temperature for 60 minutes (shaker), Incubation with antigen: each well was incubated with $E^{RNS}$ containing lysate (lysate of insect cells infected with recombinant baculovirus or lysate of culture cells infected with pestiviruses) diluted with blocking solution; incubation at room temperature for 90 minutes (shaker), Incubation with hybridoma supernatant: supernatant (10 to 25 μl) was diluted with blocking solution; incubation at room temperature for 120 minutes (shaker), Incubation with detection antibody at room temperature for 90 minutes (shaker) followed by incubation with peroxidase substrate.

Example 2

Binding Characteristics of Monoclonal Antibody 50F4

The anti-$E^{RNS}$ producing hybridoma culture 50F4–10-INT (ECACC no. 99020505) was selected for recloning and examined for its binding characteristics.

(a) The monoclonal antibody 50F4 has been primarily characterised by ELISA (as described above) using extracts from cells infected with a panel of different pestiviruses. The Moab shows reaction with the $E^{RNS}$ protein of all strains used (see Table 1). The selected pestivirus strains cover all of the four described species of pestiviruses (CSFV, BVDV-1, BVDV-2 and BDV) and most of the different subgroups within the species.

(b) The Moab recognises $E^{RNS}$ by immunoblotting. The reactivity is restricted to protein, which is separated under non-reducing conditions. If the protein is separated under reducing conditions, the Moab does not recognise $E^{RNS}$ indicating that the conserved antigen determinant reactive with the Moab is a conformational antigen determinant.

TABLE 1

Reaction of Moab 50F4 with different pestiviruses

| Antigen | 50F4 |
|---|---|
| non infected PK15 cells | − |
| CSFV-Alfort Tübingen | + |
| CSFV-Schweinfurt | + |
| CSFV-Siegburg | + |
| CSFV-Riems | + |
| CSFV-Weilburg | + |
| CSFV-Rhön | + |
| CSFV-Alfort/187 | + |
| CSFV-Henken | + |
| CSFV-Celle | + |
| CSFV-Belgien | + |
| CSFV-Polen | + |
| CSFV-Brescia | + |
| CSFV-Eystrup | + |
| CSFV-Duvaxin | + |
| CSFV-Lothringen | + |
| CSFV-iffa | + |
| CSFV-Paderborn | + |
| non infected MDBK cells | − |
| BDV-X818 | + |
| BDV-Frijters | + |
| BDV-X878 | + |
| BDV-Deer GB | + |
| BVDV-Osloss | + |
| BVDV-Rispoval | + |

TABLE 1-continued

Reaction of Moab 50F4 with different pestiviruses

| Antigen | 50F4 |
|---|---|
| BVDV-ncp7 | + |
| BVDV-Oregon | + |
| BVDV-V85 | + |
| BVDV-Singer | + |
| BVDV-5322/97 | + |
| BVDV-Gi I | + |
| BVDV-Gi IV | + |
| BVDV-890 | + |

Example 3

Antigen ELISA with Moab 50F4 as Capture Antibody

The antigen ELISA was carried out according to standard protocols:

A.

Procedure:

Coating: Each well of the ELISA plates were coated with 5 μl of supernatant of Moab 50F4 in 45 μl PBS; coating was performed overnight at 4° C., Blocking: Each well received 200 μg of blocking solution (2% skim milk in PBS/0.05% Tween 20); incubation at room temperature for 60 minutes (shaker), Incubation with samples: Each well received 50 μl blocking solution and 100 μl sample (serum/plasma); incubation at room temperature for 180 minutes (shaker), Incubation with biotinylated rabbit antiserum against $E^{RNS}$ diluted 1:1000 in blocking solution, 50 μl per well; incubation at room temperature for 90–120 minutes (shaker), Incubation with peroxidase conjugated streptavidin diluted 1:2000 in blocking solution, 50 μl per well; incubation at room temperature for 45–60 minutes (shaker), Between each of the above described steps the plates are carefully washed 4 to 5 times with ELISA wash buffer (20 mM Tris-HCl pH 7.4/300 mM NaCl/2.5 mM KCl/0.05% Tween 20).

Incubation with TMB substrate; 50 μl per well; stop of enzyme reaction with 50 μl stop solution per well.

Result:

Initially we used an IgG preparation from a polyclonal monospecific antiserum against $E^{RNS}$ as a capture antibody, and in a labelled form also as detecting antibody in an ELISA for the identification of persistently infected cattle. Using these reagents we were not able to discriminate negative and positive samples from cattle, since we obtained false positive results (see FIG. 1, sample #1489). This problem could be solved by replacing the polyclonal monospecific serum against $E^{RNS}$ as capture antibody by the monoclonal antibody 50F4. FIG. 1 shows the result of an ELISA using the same samples but the two different set-ups of the test. Obviously sample #1489 did not anymore give rise to a false positive result. In this experiment, detection of bound antigen is performed with the labelled polyclonal monospecific antiserum against $E^{RNS}$, but it may be appropriate to replace the polyclonal antiserum in the detecting phase by a Moab.

B.

Procedure:

In a further assay using the materials as described under A., 96 well plates were coated with 5 µl of Moab 50F4/well in coating buffer (50 µl/well) for 1h at 37° C. After repeated washing (4x) the plates were blocked with blocking buffer (200 µl well) for 1h at room temperature. After removal of the blocking buffer and repeated washings (3x) plasma samples were added (100 µl/well) and incubated for 1h at room temperature.

After repeated washing (3x) biotinylated rabbit anti-$E^{RNS}$ serum was added (100 µl/well) at a dilution of 1:2000 and incubated for 1h at room temperature. This was followed by washing steps (3x) and addition of streptavidine-horseradish peroxidase conjugate (1:2000 in PBS). After incubation for 45 min. at room temperature plates were washed (3x) and ready to use TMB substrate was added (100 µl/well). The reaction was stopped after 5–10 min. by addition of 50 µl stop solution.

The plates were read in an ELISA reader equipped with a 450/620 nm filter combination.

Result:

135 randomly selected blood samples were tested. From the blood samples plasma was prepared by centrifugation and employed in the $E^{RNS}$ ELISA. The remaining blood samples were further processed for virus isolation in cell culture using standard procedures. When results from plasma samples tested in the $E^{RNS}$ ELISA were compared to the respective results from virus isolation ("gold standard") a specificity of 100% and a sensitivity of 89% were calculated for the present ELISA (Table 2).

TABLE 2

|  | Virus isolation | |
| --- | --- | --- |
| ELISA | + | − |
| + | 16 | 0 |
| − | 2* | 117 |

*both virus isolates were recognised by Moab 50F4 when cell culture supernatant was used in the test.

Example 4

Antigen ELISA with Moab 50F4 as Detector Antibody

A.

Procedure:

In a comparative test the specificity and sensitivity of an antigen ELISA according to the present invention and a commercially available antigen ELISA (BVDV Antigen Test Kit FOR SERUM; available from Syracuse Bioanalytical, Inc, Ithaca, N.Y., USA; PCT application WO 99/15900) were examined. The latter assay uses the Moab 15C5 as an $E^{RNS}$-specific capture antibody. The detector system is a polyclonal goat anti-BVDV antibody in conjugation with an HRP-anti-goat conjugate. The assay is carried out according to the instructions enclosed with the test kit.

The assay according to the invention is carried out as described in the test kit CHEKIT-BVD-Virus-II available from Dr. Bomnmeli A G, Bern, Switzerland. This test uses affinity purified rabbit-anti-$E^{RNS}$ antibodies as capture antibody and the HRP-conjugated Moab 50F4 as the detector system.

Result:

23 positive and 23 negative (according to virus isolation) serum samples were tested. The assay according to the invention performed almost the same as the "gold standard" and was slightly better than the comparative test in that it identified one more positive sample and features improved MV-parameters (Table 3):

TABLE 3

| Virus isolation (gold standard) | Antigen ELISA based on Moab 50F4 | Antigen ELISA based on Moab 15C5 |
| --- | --- | --- |
| 23 positive | 22 pos. 1 neg. | 21 pos. 2 neg. |
| 23 negative | 23 neg. | 23 neg. |
| MV* positives | 3.069 | 1.499 |
| MV* negatives | 0.157 | 0.192 |

*MV is the average of the mean value of the ELISA read-out

B.

Procedure:

In a comparative experiment the assay according to the present invention as described under A. (CHEKIT-BVD-Virus-II) was compared with the prior art test kit CHEKYF-BVD-Virus (Dr. Bommeli A G, Bern, Switzerland). The latter test is also an antigen detection assay, but is based on the detection of the BVDV NS2/3 antigen in leukocyte preparations. This test uses a NS2/3 specific Moab C16 as a capture antibody and swine anti-BVDV antibody conjugated with HRP as the detector system.

Results:

It was found that in the assay according to the invention a substantial higher number of positive samples (as determined by virus isolation) was indeed identified as positive if compared with the prior art assay based on the NS2/3 antigen ELISA (Table 4).

TABLE 4

| Virus isolation (gold standard) | Antigen ELISA based on $E^{RNS}$ antigen detection | Antigen ELISA based NS2/3 antigen detection |
| --- | --- | --- |
| 343 positive | 327 pos. 16 neg. | 308 pos. 35 neg. |
| 263 negative | 254 neg. 9 pos. | 261 neg. 2 pos |

Legend to the Figures

FIG. 1 shows the result of two antigen ELISAs with two different capture antibodies.

Left: polyclonal anti-$E^{RNS}$ antiserum

Right: Moab 50F4

Sample#1489: serum from non-infected animal

Sample #11137: serum from non-infected animal

Sample #872: serum from persistently-infected animal

We claim:

1. A monoclonal antibody which is capable of specifically binding to an $E^{RNS}$ antigen determinant of a Pestivirus which either is or cross-competes with a monoclonal antibody secreted by hybridoma cell line 50F4, deposited at the ECACC under accession no. 99020505.

2. A hybridoma cell line capable of secreting a monoclonal antibody claim 1.

3. A method for the diagnosis of Pestivirus infection in animals, comprising contacting a test sample contacted with a monoclonal antibody according to claim 1.

4. The method according to claim 3, wherein a test sample of cattle is examined for the presence of BVDV antigens or antibodies.

5. The method according to claim 3, wherein the test sample is examined for the presence of Pestivirus antigens and comprises the steps of:
   (i) incubating the test sample with the monoclonal antibody,
   (ii) allowing the formation of an antibody-antigen complex, and
   (iii) detecting the presence of the antibody-antigen complex.

6. The method according to claim 3, wherein the monoclonal antibody is coated on a solid support.

7. The method according to claim 3, wherein the test sample is serum or plasma of an animal suspected of being infected with the Pestivirus.

8. The method according to claim 3, which is an enzyme-linked immunosorbent assay (ELISA).

9. An assay kit for the detection of a Pestivirus antigen, comprising a monoclonal antibody according to claim 1 and means for detecting whether the monoclonal antibody is bound to the antigen.

10. The assay kit of claim 9, wherein the Pestivirus antigen is a BVDV antigen.

* * * * *